United States Patent
Besnard et al.

(10) Patent No.: US 8,030,100 B2
(45) Date of Patent: Oct. 4, 2011

(54) CHEMICAL SENSOR

(75) Inventors: Isabelle Besnard, Tübingen (DE); Tobias Vossmeyer, Esslingen (DE); Akio Yasuda, Esslingen (DE); Marko Burghard, Magstadt (DE); Ulrich Schlecht, Stuttgart (DE)

(73) Assignee: Sony Deutschland GmbH, Cologne (DE)

( * ) Notice: Subject to any disclaimer, the term of this patent is extended or adjusted under 35 U.S.C. 154(b) by 376 days.

(21) Appl. No.: 12/412,148

(22) Filed: Mar. 26, 2009

(65) Prior Publication Data

US 2009/0227059 A1    Sep. 10, 2009

Related U.S. Application Data

(60) Division of application No. 11/353,378, filed on Feb. 14, 2006, now Pat. No. 7,531,136, which is a continuation-in-part of application No. 10/496,380, filed as application No. PCT/EP02/13309 on Nov. 26, 2002, now abandoned.

(30) Foreign Application Priority Data

Nov. 26, 2001    (EP) .................................... 01128064

(51) Int. Cl.
   *G01R 31/26*      (2006.01)
   *G01N 27/00*      (2006.01)
   *B82B 1/00*      (2006.01)
   *G01N 7/00*      (2006.01)

(52) U.S. Cl. ............ 438/17; 438/14; 438/18; 422/82.01; 422/82.02; 422/82.03; 422/83; 422/98; 977/815; 977/880; 977/902; 977/920; 977/921; 436/149; 436/150; 436/151; 73/23.2; 73/23.4; 73/24.04; 73/29.01; 73/31.06

(58) Field of Classification Search .................... None
See application file for complete search history.

(56) References Cited

U.S. PATENT DOCUMENTS 5,801,297 A    9/1998    Mifsud et al.
(Continued)

FOREIGN PATENT DOCUMENTS

DE      36 04 594 A1    8/1987
(Continued)

OTHER PUBLICATIONS

Muster, J., et al., "Electrical Transport Through Individual Vanadium Pentoxide Nanowires," Advanced Materials, 12(6): 420-24, 2000 (XP-000923871).

(Continued)

*Primary Examiner* — Jill Warden
*Assistant Examiner* — Neil N Turk
(74) *Attorney, Agent, or Firm* — Oblon, Spivak, McClelland, Maier & Neustadt, L.L.P.

(57) ABSTRACT

The application relates to a chemical sensor device comprising a substrate (1), a sensor medium (3) formed on the substrate, the sensor medium comprising one-dimensional nanoparticles, wherein the one-dimensional nanoparticles essentially consist of a semiconducting $A_xB_y$ compound, e.g. $V_2O_5$ and detection means (2) for detecting a change of a physical property of the sensor medium e.g. conductivity. The porosity of the sensor medium supports a fast access of the analyte to the sensing material and therefore a fast response of the sensor. The selectivity and sensitivity of the sensor can be tailored by doping the one-dimensional nanoscale material with different dopants or by varying the dopant concentration. Sensitivity of the sensor device to an analyte, preferably an amine, can be increased by increasing relative humidity of the sample to at least 5%.

5 Claims, 12 Drawing Sheets

U.S. PATENT DOCUMENTS

| | | | |
|---|---|---|---|
| 6,387,329 | B1 | 5/2002 | Lewis et al. |
| 6,759,010 | B2 | 7/2004 | Lewis et al. |
| 2004/0180203 | A1 | 9/2004 | Yadav et al. |

FOREIGN PATENT DOCUMENTS

| | | |
|---|---|---|
| JP | 62-192643 | 8/1987 |
| JP | 9-21773 | 1/1997 |
| JP | 9-512632 | 12/1997 |
| JP | 11-248660 | 9/1999 |
| JP | 11-352087 | 12/1999 |
| WO | WO 95/30143 | 11/1995 |
| WO | WO 98/26871 | 6/1998 |
| WO | WO 01/44796 | 6/2001 |

OTHER PUBLICATIONS

Kong, J., et al. "Nanotube Molecular Wires as Chemical Sensors," Science, 287: 622-25, 2000 (XP-002197818).

Pan, Z.W., et al., "Nanobelts of Semiconducting Oxides," Science, 291: 1947-49, 2001 (XP-002197819).

Bondarenka, V., et al., "Conductance Versus Humidity of Vanadium-Metal-Oxygen Layers Deposited from Gels," Phys. Stat. Sol., 169: 289-94, 1998 (XP-002235357).

CHEMICAL SENSOR

This application is a divisional of, and claims the benefit of priority under 35 U.S.C. §120 from, U.S. application Ser. No. 11/353,378, filed Feb. 14, 2006, which is in turn a continuation-in part of U.S. application Ser. No. 10/496,380, filed Nov. 18, 2004, which is a 371 of PCT/EP02/13309 filed on Nov. 26, 2002, published on Jun. 5, 2003 under publication number WO 03/046536 A1 which claims priority benefits from European Application No. 01 128 064.1, filed Nov. 26, 2001, the entirety of each of which is incorporated herein by reference.

BACKGROUND

1. Field of the Invention

The invention relates to a chemical sensor device, a method for obtaining such chemical sensor device and a method for detecting analyte by using said chemical sensor device.

2. Description of Related Art

In recent years much effort has been made to develop devices, which mimic the sense of smell or taste. Such devices, which are usually called electronic noses and electronic tongues, respectively, would be well suited for a broad variety of applications, such as entertainment robots, identification systems, quality control systems, environmental monitoring, and medical diagnostics. However, up to now only a limited number of electronic nose devices have been marketed. Although these devices are capable of identifying or classifying some "odor" samples, further improvements are necessary to fulfill the needs for many advanced applications mentioned above. These applications often require higher sensitivity, higher discrimination capability, faster response, better stability, and lower power consumption. Since such features strongly depend on the characteristics of the chemical sensors used in the device, there is a strong demand for improved sensors meeting the requirements for advanced e-nose and e-tongue applications. An overview of sensor principles currently under development is given in J. W. Gardner and P. N. Bartlett, Electronic noses—Principles and applications, 1999, pages 67-116 Oxford University Press, Oxford.

There are several gas sensors available on the markets among which are metal oxide sensors, often referred to as Tagushi sensors. They are composed of metal oxide(s) having a porous form, generally doped with a metal. They are operated at elevated temperatures of 100 to 600° C. in order to allow combustion of the analyte at the metal oxide surface, inducing a change of oxygen concentration and therefore a change in conductance. Metal oxide sensors are generally employed as single device to detect toxic or flammable gases. They can also be employed as arrays for electronic noses, but their use for odor recognition was up-to-now limited by the lack of selectivity.

J. Kong, N. R. Franklin, C. Zhou, M. G. Chapline, S. Peng, K. Cho and K. Dai, Science, 2000, 287, 622-625 describe chemical sensors based on individual single-walled carbon nanotubes (SWNTs). Upon exposure to gaseous molecules such as NO2 or NH3, the electrical resistance of a semiconducting SWNT is found to change by up to three orders of magnitude within several seconds of exposure to analyte molecules at room temperature. The chemical sensors are obtained by controlled chemical vapour deposition growth of individual SWNTs from patterned catalyst islands on $SiO_2$/Si substrates. Sensor reversibility is achieved by slow recovery under ambient conditions or by heating to high temperatures. After e.g. the $NO_2$-flow is replaced by pure Ar, the conductance of the SWNT sample slowly recovers with a typical recovery time of about 12 hours at room temperature.

Z. W. Pan, Z. R. Dai and Z. L. Wang, Science, 2001, 291, 1947-1949, describe the synthesis of ultralong beltlike nanostructures, so-called nanobelts, of semiconducting oxides of zinc, tin, indium, cadmium, and gallium by evaporating the desired commercial metal oxide at high temperatures. The as-synthesized oxide nanobelts are pure, structurally uniform, and single crystalline, and most of them are free from defects and dislocations. They have rectangle cross section with typical width of 30 to 300 nanometers, width-to-thickness ratios of 5 to 10, and lengths of up to a few millimeters. A possible use of doped nanobelts as nanosize sensor is suggested.

V. Bondarenka, S. Grebinskij, S. Mickevicius, H. Tsardauskas, Z. Martunas, V. Volkov and, G. Zakharova, Phys. Stat. Sol., 1998, A 169, 289-294, have investigated the influence of humidity on the electrical properties of polyvanadium acid xerogels and xerogels based on poly-vanadium acid where vanadium is partly substituted by molybdenum or titanium. The conductance of thin-film samples increases with an increase in humidity as an exponential function and therefore those films are suitable for the fabrication of humidity sensors. Thin films of the vanadium-metal-oxygen materials were produced by the sol-gel technology. The vanadium pentoxided powder and the other components were dissolved in hydrogen peroxide at 273K. Then the solution was heated in an open beaker at 353K for one/two hours. The obtained gels were deposited by a screen-printing method on substrates and baked at 333K in air. All compounds such obtained have a layered structure with inter-layer distances of 11.1 to 11.5 angstroms. The amount of water contained in the compounds depends on the relative humidity RH and increases with an increase in RH.

S. Capone, R. Rella, P. Siciliano and L. Vasanelli, Thin Solid Films, 1999, 350, 264-268, investigated the physical and gas sensing properties of bulk material $V_2O_5$ and $WO_3$ thin films. Gas-sensitive films of vanadium oxide and tungsten oxide were prepared by means of sputtering technique in a thickness of about 200 mm. Samples for gas testing were placed onto a heated sample holder and exposed to different gas concentrations. For both materials at high temperatures a strong exponential dependence of the electrical conductivity on the temperature was observed. Upon exposure to NO gas an increase of the electrical resistance of the films was observed. $WO_3$-based sensors exhibited higher sensitivity values than $V_2O_5$ ones. In addition, tungsten oxide thin films were also able to detect very low concentrations of NO in the sub-ppm range. $V_2O_5$ could be used for detection of high concentration of NO, up to a range of 50-500 ppm.

Z. A. Ansari, R. N. Kareka and R. C. Aiyer, Thin Solid Films, 1997, 305, 330-335 describe a humidity sensor using planar optical waveguides with claddings of various oxide materials, among others bulk-$V_2O_5$. The planar waveguides were fabricated on a soda-lime glass substrate using an ion-exchange process. Films of porous semiconducting oxides were screen printed on the waveguide surface. The relative humidity (RH) was varied from 3 to 98%. At a cladding length of 3 mm and a cladding thickness of 25 μm $V_2O_5$ exhibited a response time of 5 secs. and a recovery time of 30 min. A hysteresis of 8% is observed for $V_2O_5$ cladding.

R. Rella, P. Siciliano, A. Cricenti, R. Generosi, L. Vanzetti, M. Anderle and C. Coluzza, Thin Solid Films, 1999, 349, 254-259, studied the physical properties and gas-surface interaction of bulk vanadium oxide thin films. Thin films of vanadium oxide were prepared by means of r.f. reactive sputtering. For evaluation of sensing properties the films were electrically tested in presence of different gases. Films grown with 15% oxygen in an Ar—$O_2$-mixture exhibited best sensing properties, giving a maximum response at a working temperature ranging between 280 and 300° C.

In most cases vanadium pentoxide is only a secondary component in the sensitive coating employed in combination with a more sensitive material, e.g., $WO_3$. X. Wang, N. Miura and N. Yamazone, Sensors and Actuators, 2000, B66, 74-76, report on $WO_3$-based sensing materials for $NH_3$ and NO detection. Gas sensing materials loaded with 1 wt.-% metal oxides were prepared. The sensing properties of these materials towards $NH_3$ and NO were better than of sensing films of pure $WO_3$.

The use of vanadium pentoxide films as temperature sensor is described by Z. S. El Mandouh and M. S. Selim, Thin Solid Films, 2000, 371, 259-263. The vanadium pentoxide films were prepared by an inorganic sol-gel method. The temperature coefficient of resistance, $\beta_T$, is 2% $K^{-1}$, which indicates, that $V_2O_5$ can be used as a thermoresistor.

WO98/26871 discloses nanotubes made from transitions metal oxides, preferably from a vanadium oxide of variable valence. The nanotubes show oxidation-reduction activities and are particularly suited as an active material for catalytic reactions. In the experimental part synthesis of vanadium oxide nanotubes and the structure of the nanotubes obtained is described.

WO01/44796 discloses a nanotube device comprising at least one nanotube, preferably a carbon nanotube, which is electrically connected with its ends to first and second conducting elements. The nanotube device may be used as a chemical or biological sensor. To tune the sensitivity of the device to a variety of molecular species the nanotubes may be modified by coating, or decorating with one or more sensing agents, so as to impart sensitivity to a particular species in its environment. The nanotubes may also be formed from other materials than carbon, e.g. silicon. Detection of various analytes is demonstrated in the experiments. Experiments were done on $NO_2$ and $NH_3$ gas, thioles, $H_2$, CO and avidin (a protein). Modification of the sensitivity by depositing metal particles, e.g. gold, platinum of nickel, metal oxides, e.g. $TiO_2$, or biological species on the sensing agent is also described.

Several types of sensors can be employed at room temperature and show good selectivity to organics. The most commonly encountered are conducting polymer chemiresistors polymer based SAW (Surface Acoustic Wave) and BAW (Bulk Acoustic Wave) devices. However, some of these sensors suffer from low sensitivity like for example conducting polymer chemiresistors to gases. Devices based on mechanical transducers like cantilever and BAW devices are harder to incorporate into integrated circuits than the ones based on electrical transducers. For optical detection based sensors, the complexity of the transducer may be a limiting factor, especially when miniaturization is considered. Concerning electrochemical cells, they are of limited use in the gas sensor domain but are gaining importance for electronic tongues.

A general problem in the use of sensors is humidity. Found in a large majority of samples it decreases the detection capabilities. The first reason is related to the fact that water will influence the analyte partitioning in the sensor medium or weaken the interactions of the analyte with the sensor medium. An example is the detection of an aroma of wine. One has to be capable of detecting traces of an aromatic compound among a matrix containing large amounts of water and alcohol. A second problem is that a change in humidity can be seen as a false detection. For example in the case of CO detection, a 20% change in relative humidity should not be interpreted as a 50 ppm CO.

A way to minimize the humidity problem is to dry the analyte. One can dehydrate the sample itself before analysis, for example dehydrating cheese before sensory analysis. The drawback is that the smell may denature during the process because volatiles are removed or decomposed. The headspace of the sample can also be dried before reaching the detector. This can for example be performed using a nafion filter. Water will be filtered off but some components of the analyte, like alcohols, will also be removed, partially or completely. Water can also be eliminated by separating the different chemicals of a sample using techniques like gas chromatography or similar techniques.

Only a limited number of reports exist where humidity is of advantage, meaning the sensors show an increase of sensitivity with increasing humidity. Kappler, J.; Tomescu, A.; Barsan, N.; Weimar, U.; Thin Solid Films 2001, 391, 186-191, report on an increase of sensitivity of $SnO_2$ gas sensors operated at elevated temperature toward CO with increasing humidity. The sensor's response ($R_{air}/R_{co}$) increased from 5 to 30 by increasing the humidity from 0 to 50% relative humidity. Sadaoka, Y.; Sakai, Y.; Murata, Y. U.; Sensors and Actuators 1993, B 13-14, 420-423 report a similar behavior of an optical sensor based on calcein-poly(acrylonitrile) in the case of ammonia detection. The sensitivity increased when $I/I_0$ (optical intensity ratio) decreased from 0.95 to 0.83 under dry air and 50% relative humidity, respectively. Another illustration is based on host molecules (tecton, DM 189) deposited on a mass-sensitive device (Boeker, P.; Horner, G.; Rosler, S. Sensors and Actuators 2000, B 70, 37-42). The response to 100 ppm ammonia (in Hertz) is double at 20.000 ppm water (saturated, humidity) compared to the response in dry air.

Amines are found in many foodstuffs, for example in wine, fish, cheese or meat. Amines can be for example indicators of fish freshness. Amines can also give some information on the health status of a person. There is therefore a need for amine sensors in the food industry and for medical applications. These sensors should be highly sensitive to the target preferably as well as show no significant decrease in sensitivity when humidity is present. An electronic nose comprising such sensors is therefore of great interest.

Some amine gas sensors are commercially available. For example electrochemical cells are offered on the market that are specific to a given amine, and that for a wide range of amines. The detection limit is around 2.5 to 5 ppm, depending on the amine. The main problem appears to be the size, which is in the centimeter scale. Metal oxide sensors can also detect ammonia, with a detection limit of about 25 ppm, but they suffer from their high power consumption and a low selectivity to amines.

SUMMARY OF THE INVENTION

It is an object of the invention to provide a chemical sensor device with a high selectivity towards analytes, a high sensitivity and a high stability in performance which can be operated at a temperature close to room temperature and has low power consumption.

To solve this object, the present invention provides a chemical sensor device, comprising a substrate, a sensor medium formed on the substrate, the sensor medium comprising one-dimensional nanoparticles, wherein the one-dimensional nanoparticles essentially consist of a semiconducting $A_xB_y$ compound, wherein the semiconducting $A_xB_y$ compound is selected from the group, consisting of II-VIsemiconductors, III-V-semiconductors, semiconducting metal oxides (B=O), semiconducting metal sulfides (B=S), semiconducting metal phosphides (B=P), metal nitrides (B=N), semiconducting metal selenides (B=Se) and semiconducting metal tellurides (B=Te); and detection means for detecting a change of a physical and/or chemical property of the sensor medium.

The semiconducting metal compounds have different selectivities towards a target analyte. The material of the one-dimensional nanoparticles used for assembling the sensor device are therefore selected depending on the analyte to be detected. The semiconducting $A_xB_y$ compound may be a binary compound wherein A and B are a single element, respectively. Examples are $SnO_2$ and MgO. Further also ternary or quaternary compounds may be used, e.g. GaAs/P. Preferably is x>0 and y>0.

Preferably A is at least one element selected from the group consisting of V, Fe, In, Sb, Pb, Mn, Cd, Mo, W, Cr, Ag, Ru and Re. Preferably B is at least one element selected from the group consisting of O, S and Se.

The metal (compound A) in a semiconducting $A_xB_y$ compound may be present in a single oxidation state. Preferably at least one element (A or B) is present in different oxidation states in a shingle semiconducting $A_xB_y$ compound. Most preferred Element A is present in different oxidation states. The ratio between the two oxidation states preferably ranges between 0.001 and 0.1. When using e.g. $V_2O_5$ as a material of the one-dimensional nanoparticles vanadium may be present in the $V^{4+}$ as well as in the $V^{5+}$ state. In the case of $V_2O_5$, the mixed valence is due to defects in the structure.

Therefore, the mixed valence is not obvious from the formula. Another example for a mixed valence compound is $Fe_3O_4$ where the stoichiometric indexes indicate that there are. $Fe^{II}$ and $Fe^{III}$ in the material and the ratio of Fe ions in the oxidation states II/III is equal to 0.5. Further examples for elements forming e.g. oxides and sulfides where the element can be of different oxidation state are cobalt, chromium, lead, titanium, rhenium and molybdenum. Further illustrations of elements giving in the case of oxides different oxidation states are aluminum, gallium, germanium or iridium. Within one given material, two different oxidation states can be encountered (mixed valence). Sn is as $Sn^{II}$ in SnO, as $Sn^{IV}$ in $SnO_2$ and as $Sn^{II}$ and $S^{IV}$ in $Sn_3O_4$. Similarly, Sb is found as $Sb^{III}$ and $Sb^{IV}$ in oxide, as well as (III and V) in $Sb_2O_5.xH_2O$. Chromium can form oxides with the oxidation states II, III, IV and VI, as well as (II and III) in $Cr_3O_4$. Similar behavior is known for manganese (II, III, IV, VII, and (II and III) in $Mn_3O_4$) as well as silver (I and III in $Ag_2O_3$).

The mixed valence can also be introduced by defects, e.g. by a dopant or an impurity. By providing an element in different oxidation states the charge carrier concentration can be controlled and therefore the electrical conductivity of the semiconducting $A_xB_y$ compound at room temperature may be enhanced. By creating possible reaction sites, for example by introducing defects, the sensitivity of the sensor may be enhanced.

The one-dimensional nanoparticles used as the sensitive medium in the sensor device according to the invention have a much larger extension in a longitudinal direction than in directions perpendicular thereto. Usually the nanoparticles have dimensions in the micrometer scale in a longitudinal direction and in the nanometer scale in both directions perpendicular thereto. Preferably the one-dimensional nanoparticles have a length of less than 100 µm, especially preferred less than 15 µm, most preferred between 100 and 15 µm, and a cross section of less than 100.000 $nm^2$, preferably less than 5000 $nm^2$, especially preferred less than 50 $nm^2$. The length of the one-dimensional nanoparticles can conveniently be controlled by the reaction time during the synthesis of the one-dimensional nanoparticles. The one-dimensional nanoparticles have the shape of a fiber or filament and therefore do not easily self-organize to form a close-packed arrangement as for example nanoparticles which have a spherical shape. Therefore voids within the sensor medium are increased allowing a better access of the analyte to the one-dimensional sensing material. The sensor medium of the sensor device according to the invention provides a large surface area accessible to the analyte which enables a high sensitivity of the sensor medium and a fast response of the sensor device.

The one-dimensional nanoparticles are present in the sensor medium as individual particles. It is sufficient to stabilize the sensor medium just by physical interactions and to deposit the one-dimensional nanoparticles on a substrate surface. To increase mechanical stability of the sensor medium the one-dimensional nanoparticles may be interlinked by e.g. bifunctional ligands or may be embedded in a matrix.

The one-dimensional nanoparticles used in the sensor device according to the invention are made from a semiconducting material essentially consisting of a semiconducting $A_xB_y$ compound. Depending on the nature of the components A and B of the semiconducting $A_xB_y$ compound the one-dimensional nanoparticles have different selectivity towards a given analyte compared to the carbon-SWNT based sensors described by J. Kong et al. loc. cit. Methods for obtaining one-dimensional nanoparticles, as used in the sensor device according to the invention, are well established. The one-dimensional nanoparticles can easily be modified in their composition, e.g. by addition of a dopant, and therefore the sensor device can be tailored to a target analyte.

The chemical sensor device according to the invention can be operated close to room temperature and therefore has low power consumption because generally no heating of the sensor medium is necessary. This also enables an easy operation of the sensors according to the invention. Usually the sensor is operated at temperatures below 100° C., preferably below 50° C. especially preferred at room temperature. The sensors can be produced at low costs and also can be miniaturized to form part of integrated circuits.

The one-dimensional nanoparticles may be hollow or filled and may e.g. have the form of a nanotube or a nanowire. Filled one-dimensional nanoparticles are preferred. Further the one-dimensional nanoparticles may have various shapes of cross sections, e.g. may have a round (circular) or rectangular cross section. The one-dimensional nanoparticles may then have the form of a nanowire or a nanobelt. Nanobelts are especially preferred as sensing material. The sensor medium may also comprise bundles of one-dimensional nanoparticles.

The synthesis of one-dimensional nanoparticles formed of III-VI-semiconductors or III-V-semiconductors is e.g. described by X. Duan and C. M. Lieber, Adv. Mat, 2000, 12, 298-301. Binary Group III-V materials that may be used for the sensor according to the invention are e.g. GaAs, GaP, InAs and InP. Ternary III-V materials are GaAs/P or InAs/P, examples for binary II-VI compounds are ZnS, ZnSe, CdS, and CdSe. One-dimensional nanoparticles have been prepared from the above-mentioned semiconducting materials in bulk quantities with high purity. Nanowires for examples can be prepared using the laser assisted catalytic growth (LCG) method.

One-dimensional nanoparticles of semiconducting metal oxides can be prepared by a method described by Z. W. Pan et al. loc. cit. Semiconducting metal oxides that can be used as a source for the preparation of one-dimensional nanoparticles used in the sensor device according to the invention are e.g.

$Ga_2O_3$, $SnO_2$, $In_2O_3$, $PbO_2$, MgO, $Fe_2O_3$, $W_{18}O_{49}$, and $GeO_2$. One-dimensional nanoparticles consisting of semiconducting metal sulfides may be prepared from $MoS_2$, $NbS_2$, $TaS_2$, $TiS_2$, $WS_2$, $W_{0.7}Mo_{0.2}C_{0.1}S_2$. A suitable method to prepare $MoS_2$ and $WS_2$ as well as BN nanotubes is e.g. described by M. M. Nath, A. Govindaraj and C. N. R. Rao, Adv. Mat., 2001, 13, 283-286.

Patzke, G. R.; Krumeich, F.; Nesper, R. Angew. Chem. Internat. Edit. 2002, 41, 2446-2461 reported on the formation of nanotubes, and nanorods of oxides (e.g. $Fe_2O_3$, $Fe_3O_4$, $In_2O_3$, $Sb_2O_3$, $SnO_2$, $TiO_2$ and $SiO_2$). The synthesis of $Si_3N_4$-nanoparticles has been described by Han, W.; Fan, S.; Li, Q.; Hu, Y. Science 1997, 277, 1287-1289; Remskar, M.; Mrzel, A.; Skraba, Z.; Jesih, A.; Ceh, M.; Demsar, J.; Stadelmann, P.; Levy, F.; Mihailovic, D. Science 2001, 292, 479-481 described the synthesis of one-dimensional nanoparticles made from GaSe.

One-dimensional nanoparticles can be prepared with a wide range of compounds using a porous template, e.g. a porous polycarbonate membrane (Kovtyukhova, N. I.; Mallouk, T. E. Chem. Eur. J. 2002, 8, 4355-4363; Mbindyo, J. K. N.; Mallouk, T. E.; Mattzela, J. B.; Kratochvilova, I.; Ravazi, B.; Jackson, T. N.; Mayer, T. S. J. Am. Chem. Soc. 2002, 124, 4020-4026) or a one-dimensional template. Examples of one-dimensional templates are carbon nanotubes or organic fibers. The template can be removed via the appropriate technique, for example thermal decomposition or etching, leaving the required one-dimensional nanoparticles. Details towards the growth of one-dimensional nanoparticles are given e.g. in Caruso, R. A.; Schattka, J. H.; Greiner, A. Adv. Mat. 2001, 13, 1577-1579.

The materials mentioned above can be used in pure form or in combination with each other. For example it is possible to use one-dimensional nanoparticles made of pure $V_2O_5$. The physical characteristics of the one-dimensional $V_2O_5$ may be modified by adding a further material, e.g. $WO_3$, to the one-dimensional $V_2O_5$-material. Further different one-dimensional nanoparticles made of different semiconducting materials may be used within a single sensor medium of the chemical sensor according to the invention. The sensor medium then contains e.g. a first one-dimensional nanoparticle made of a first semiconducting $A_xB_y$ compound and a second one-dimensional nanoparticle made of a second semiconducting $A_xB_y$ compound.

Preferably the semiconducting one-dimensional nanoparticles are made of a vanadium oxide material. Vanadium pentoxide one-dimensional nanoparticles are easily obtained by wet-chemistry, in large amounts and as pure material. They can be obtained both as nanotubes and as nanofibres or nanobelts. Vanadium pentoxide nanofibres show a suitable conductivity and can be used as coatings for chemiresistor devices.

Vanadium pentoxide nanotubes can be synthesised by templating with an amine. Such a method is described e.g. by H. J. Muhr, F. Krumeich, U. P. Chonholzer, F. Bieri, M. Niederberger, L. J. Gaukler and R. Nesper, Adv. Mat., 2000, 12, 231-234. The amine contributes to the formation of layers, which then roll to form multiwalled tubes. The amine can later be readily exchanged with neutral amine or cations by proton exchange. If no template is employed in the synthesis, the vanadium pentoxide can form belts with a rectangular cross section. Vanadium pentoxide nanobelts are well-organized solids of well defined dimension. They form ribbons of about 1-5 nm thickness, 10 nm width and more than 500 nm in length. They are n-type semiconductors produced by polymerization of ammonium(meta) vanadate on an acidic ion exchange resin. The synthesis of vanadium pentoxide nanobelts is described e.g. by O. Pelletier, P. Davidson. C. Bourgaux, C. Coulon, S. Regnault and J. Livage, Langmuir, 2000, 16, 5295-5303.

The one-dimensional nanoparticles can be employed as synthesized in an undoped form. To modify and to tune the selectivity and sensitivity of the sensors according to the invention towards a target analyte the one-dimensional nanoparticles may be doped with a dopant. Sensors with appropriate dopants are highly sensitive and allow detection of analytes at concentration levels below 1 ppm.

As a dopant ions may be used, which are incorporated in the structure or immobilized at the surface of the one-dimensional nanoparticle. This is possible by exchanging protons at the surface of the one-dimensional nanoparticle. In case of vanadium oxide most of the vanadium atoms in the one-dimensional vanadium oxide material contained in the sensor medium of the sensor according to the invention have a valence of (V), but up to 10% of the vanadium atoms can be in the valence (IV) state. However, higher amounts are also possible. To compensate for the charge defect the surface of the fibers is protonated. These protons can be readily exchanged, introducing a dopant in the film. Only part of these protons is exchanged by doping. T. Coradin, D. Israel, J. C. Badot and N. Baffier, Mat. Res. Bull., 2000, 35, 1907-1913, describe that up to 15% of the protons can be exchanged for large cation. When using vanadium oxide comprising only vanadium in the +V oxidation state hydroxy groups may be formed on the surface of the one-dimensional nanoparticle by partially hydrolysing the vanadium oxide in water. Such hydroxy groups are acidic and the protons may be exchanged by cations, e.g. $Ag^+$. Higher doping levels can be achieved by oxidation of a metal in solution. Silver doped vanadium pentoxide has been described by F. Coustier, S. Passerini and W. H. Smyrl, Solid State Ionics, 1997, 100, 247-258. The insertion of large ions can be catalyzed by a small cation. The small cation aims at partially disrupting the layered structure of the material enabling exchange by a larger cation.

The one-dimensional nanoparticles can also be doped by intercalation of neutral molecules between layers of the one-dimensional nanoparticles. This implies swelling of the structure inducing a weakening of the interaction forces between different layers of the one-dimensional nanoparticle. Such an intercalation of neutral molecules between layers of vanadium pentoxide xerogels is e.g. described by T. Coradin et al, loc. cit. and H. P. Oliveira, C. F. O. Graeff and J. M. Rosolen, Mat. Res. Bull, 1999, 34, 1891-1903. It is also possible to immobilize molecules or particles on the surface of the one-dimensional nanoparticle.

Possible dopants that may be used to dope the sensor medium are ions, like Au(III) from gold chloride or gold acetate, Au(I) or Ag(I) from the acetate or nitrate salt may also be employed. Also possible is to dip the one-dimensional nanoparticles into a solution containing the metal which is used as a dopant in solid form. The metal is then oxidized and incorporated into the one-dimensional nanoparticles. Such an incorporation of metal ions into vanadium pentoxide xerogels has been described e.g. by F. Coustier, G. Jarero, P. Passerini and W. H. Smyrl, Journal of Power Sources, 1999, 83, 9-14 who used a copper-doped $V_2O_5$ xerogel as an ingredient of a cathode material in a coin cell assembly.

Further the one-dimensional nanoparticles can be doped with organic molecules. A broad variety of organic molecules may be used as dopant The organic molecules may be hydrocarbons which may comprise one or more heteroatoms which may form polar groups. Suitable heteroatoms are e.g. oxygen, nitrogen, phosphor or sulfur. Suitable organic compounds are e.g. aromatic or aliphatic thiols, carboxylic acids, amines, phosphines, phosphine oxides, pyridine and pyridine derivatives, thiophene and thiophene derivatives, pyrrole and pyrrole derivatives. The organic molecules are adsorbed on the surface of the one-dimensional nanoparticles or intercalated between layers the one-dimensional nanoparticles thereby modifying the physical and chemical characteristics of the one-dimensional nanoparticles. For example T. Kuwahara, H. Tagaya and J. Kadokawa, Inorganic Chemistry Communications, 2001, 4, 63-65, report on the intercalation of organic dyes in layered host lattice $V_2O_5$. The intercalation of pyridine derivatives into $V_2O_5$-xerogels is described by Y. Shan, R. H. Huang and S. D. Huang, Angewandte Chemie International Edition, 1999, 38, 1751-1754. Furthermore the one-dimensional nanoparticles can be doped with conducting polymers. Such inorganic-organic hybrid microstructures are known e.g. from J. H. Harreld, B. Dunn and L. F. Nazar, International Journal of Inorganic Materials, 1999, 1, 135-146, who prepared vanadium oxide-polypyrrole hybrid aerogels. Furthermore also large organic cations can be incorporated into the structure of the one-dimensional nanoparticles. Such a material has been described. e.g. by M. Inagaki, T. Nakamura and A. Shimizu, J. Mater. Res., 1998, 13, 896-900, who prepared intercalation compounds from ammonium cations and vanadium oxide xerogels. As part of this invention incorporation of organic molecules increases the sensitivity to organic vapors. It is assumed that the organic molecules enhance the interaction with the vapor and the vapor uptake.

Also ion complexes can be used as a dopant for doping the one-dimensional nanoparticles. An ion complex that can be used as a dopant according to the invention are e.g. auriothioglucose or metal complexes with large organic molecules, like phthaloctyanins or porphyrines, H. P. Oliveria et al. loc. cit. describe the intercalation of porphyrin-copper complexes into $V_2O_5$-xerogels.

According to a preferred embodiment of the invention the sensor medium of the chemical sensor device additionally comprises a second nanoparticle material which preferably has an approximately spherical shape. The incorporation of second nanoparticles different from the one-dimensional nanoparticles into the sensor medium allows the modification of the sensor selectivity and sensor sensitivity. Metal nanoparticles can be formed by evaporation of the metal on the one-dimensional nanoparticles pre-immobilized on the substrate. Further metal nanoparticles stabilized with an organic shell can be prepared e.g. by wet chemical methods. A method for preparing such nanoparticles is e.g. described by M. Brust, J. Fink, D. Bethell, D. J. Schiffrin and C. Kiely, J. Chem. Soc., Chem. Commun., 1995, 1655-1656. This technique is applicable to a wide range of metal nanoparticles. Examples are Fe, Au, Ag, Pt, Pd, as well as some binary nanoparticles, like Fe/Pt. Such stabilized nanoparticles are soluble in common organic solvents. These nanoparticles can be immobilized on the one-dimensional nanoparticles by simply dipping the substrate pre-coated with the one-dimensional nanoparticles in the corresponding solution of the second nanoparticle. A chemical coupling between the one-dimensional nanoparticles and the second nanoparticles is possible through a bi- or polyfunctional organic linker compound. Finally, certain metal ion complexes, once in solution, produce metal particles that can be immobilized by the above-described dipping procedure. Such metal complexes are e.g. silver acetate or $AuS(CH_3)_2Cl$.

Vanadium pentoxide nanobelt-based chemical sensors are also sensitive to hydrogen gas. The sensitivity is enhanced by doping vanadium pentoxide nanobelts with a metal e.g. gold. It can be doped with nanoparticles stabilized with an organic shell, or by evaporation of a thin metal layer or with a metal salt that is converted to nanoparticles during the doping process.

According to a preferred embodiment the second nanoparticles consists of a semiconducting material. As a semiconducting material may be used e.g. II-VI and III-V semiconductors, $Cd_3P_2$ or $PbS_2$.

The sensitivity of the sensor towards a given analyte is influenced by the dopant. For detection of CO suitable dopants for vanadium pentoxide nanobelts are for example:

Platinum metal from evaporation a thin layer;
Iron(III) phthalocyanine;
Gold, metal obtained from evaporation of a thin layer or from doping with $AuS(CH_3)_2Cl$ at a high doping level.

The chemical sensor device according to the invention may use various physical and/or chemical properties to detect an analyte. In a first group, a change of electrical characteristics is detected. For example, a change in conductivity or capacity of the sensor medium may be measured. Therefore, the chemical sensor device may act as a chemiresistor or a chemicapacitor. The sensor medium can also be utilized in a configuration forming a chemidiode or a multiterminal device, such as a chemitransistor (e.g. Chem-FET). Examples of chemical sensitive transistors comprising semiconducting oligomers based on polythiophene have recently been described in the literature (B. Crone, A. Dodabalapur, A. Gelperin, L. Torsi, H. E. Katz, A. J. Lovinger, Z. Bao, Appl. Phys. Lett. 2001, 78, 2229-2231). The chemical sensor device may also be used as a mass sensitive sensor. The sensitive film comprising the one-dimensional nanoparticles is then used as a coating on a piezo-electric material to form a chemically sensitive surface acoustic wave (SAW), device or a quartz crystal microbalance (QCM) or a cantilever or any combination of such sensor types.

According to another embodiment, the chemical sensor device is used as an optical sensor. The sensor signal may then be measured as a change in reflectance, fluorescence, absorption, or scattering. In this case, the binding of analyte molecules to the sensor material leads to a change of optical properties (UV/vis and/or IR). For example, the luminescence properties may change when the analyte molecules are adsorbed to the semiconducting one-dimensional nanoparticles. This change is due to a change of the electronic states of the one-dimensional nanoparticles and/or of the close environment of the one-dimensional nanoparticles. Furthermore the one-dimensional nanoparticles can be combined with appropriate chemicals, e.g. dyes, to induce a change of optical characteristics upon interaction with an analyte.

It is also possible to utilize the sensor medium as chemically sensitive coating for fiber optics (e.g. optodes, interferometer devices). The chemical sensor device may also use changes in heat or temperature and therefore be used as a thermistor, or other thermoelectric device.

Preferably the chemical sensor device is formed as a chemiresistor, wherein the sensor medium is addressed by a pair of contacting electrodes.

The sensor medium may be deposited as a film onto interdigitated electrodes, e.g. made of Au, which were deposited onto an inert substrate, e.g. by lithographic techniques, or both electrodes may be deposited on top of the film. Also other configurations are possible. One electrode may be positioned below the sensor film and the other may be deposited on top of the sensor film. By the sorption of the analyte to the one-dimensional nanoparticles the electronic properties of the sensor are influenced resulting in a change of conductivity of the sensor film.

A heater may be provided at the sensor medium to control temperature and to heat, if required, the sensor medium for regeneration. The purpose of the heater may also be to modulate the temperature within a desired range. Performing a wavelet analysis of the signal may allow for analyte identification and quantification. A temperature sensor is also of advantage to monitor the real temperature.

The inert substrate can be made for example of $Si/SiO_2$ when the chemical sensor is integrated in an IC device. Further preferred substrates are made of glass and/or ceramics.

Several chemical sensors, which preferably have different compositions of the sensor medium and/or which are operated at different temperatures may be arranged to form a sensor array. For the selectivity and sensitivity of the sensor towards different analytes not only the nature of the dopant but also the doping level is important. Therefore an array of sensors with a gradient of concentration of dopant can be used as an array for electronic nose purposes.

The small size of the one-dimensional nanoparticles allows readily miniaturization of the devices. The chemical sensor according to the invention therefore may be miniaturized, e.g. to be used in a sensor array in an IC device.

The one-dimensional nanoparticles used in the chemical sensor device according to the invention have a quite high electrical conductivity. This is especially the case when vanadium pentoxide is used as the one-dimensional nanoparticles. Vanadium oxide comprises vanadium in the valence +IV and +V state and therefore already provides good electrical conductivity at room temperature.

The sensing action of the sensor device according to the invention can be based on different types of interactions between the analyte and the sensing material. The analyte may be adsorbed on the surface of the one-dimensional particles or may be intercalated into the structure of the sensing material. Depending on the length of the one-dimensional nanoparticles also sensor devices comprising a single one-dimensional nanoparticle may be prepared. In this case preferably a single one-dimensional nanoparticle is bridging the gap between the two electrodes. A single one-dimensional nanoparticle is sufficient to obtain a sensor medium but also several nanoparticles may be arranged in a more or less parallel arrangement. One-dimensional nanoparticles of smaller size than the gap size of the electrode pair may be arranged to form a network. The one-dimensional nanoparticles then form intersections at which the surface areas of neighboured nanoparticles are in contact with each other thereby providing a conductive path between the electrodes. The electrical transport through individual vanadium pentoxide nanowires has been described by J. Muster, G. T Kim, V. Krstic, J. G. Park, Y. W. Park, S. Roth and M. Burghard, Adv. Mater., 2000, 12, 420-424.

Surprisingly the sensitivity of the sensor device according to the invention towards an analyte increases at higher relative humidity. The sensors therefore preferably are combined with a humidity control or a humidity measuring unit. In the first case, a controlled humidity ensures a reproducible response of the sensors. In the second case, the analyte concentration can be determined using, for example, a calibration data set and taking into account the measured humidity.

The above described chemical sensor device can easily be assembled. Therefore the invention further relates to a method for forming a chemical sensor device as described above, comprising the following steps:

a) providing a substrate having a substrate surface;
b) providing one-dimensional nanoparticles essentially consisting of a semiconducting $A_xB_y$ compound, wherein A, B, x and y are as defined above;
c) coating the substrate surface with the one-dimensional nanoparticles thereby obtaining a sensor medium;
d) providing detection means for detecting a change of a physical and/or chemical property of the sensor medium.

The one-dimensional nanoparticles can be prepared by known methods. An overview on methods for obtaining one-dimensional vanadium pentoxide materials is e.g. given in J. Livage, Coordination Chemistry Reviews, 1998, 178-180, 999-1018. The characteristics of the chemical sensor according to the invention can be influenced by the synthesis conditions. The addition of a surfactant during the preparation of the one-dimensional nanoparticles introduces a high porosity as has been shown for vanadium alkoxide derived gels by S. Mege, M. Verelst, P. Lecante, E. Perez, F. Ansart and J. M. Savariault, Journal of Non-Crystalline Solids, 1998,-238, 37-44. Porosity can be as high as 75% in presence of a surfactant, and oily 5% without surfactant. In the case of devices with a relatively large number of fibers, it is of advantage to increase the porosity enhancing the diffusion rate of the analyte molecules in the sensor medium and therefore improving the response time and sensitivity.

The one-dimensional nanoparticles can be deposited on the substrate by spin-coating, drop-coating, dip-coating, brush techniques, ink jet printing technique or any other technique.

The one-dimensional nanoparticles can be aligned during deposition e.g. to bridge two chemiresistor electrodes. Alignment of one-dimensional nanoparticles is preferred when using only few nanoparticles to form a sensor medium, and allows a high reproducibility of the fabrication process. Alignment of the one-dimensional nanoparticles may be achieved by MIMIC (Micro Moulding in Capillaries) technique described by H. J. Muhr et al. loc. cit. or by applying a magnetic field. Orientation of liquid-crystalline suspensions of vanadium pentoxide ribbons by a magnetic field is e.g. described by X. Commeinhes, P. Davidson, C. Bourgaux and J. Livage, Adv. Mat, 1997, 9, 900-903.

The sensor device has an increased sensitivity towards the detection of amines at higher humidity levels. Further the sensor device shows little influence of humidity on the response towards other analytes. To obtain results with high reproducibility and/or to detect e.g. amines at very low concentration levels preferably a humidity control device and/or a humidity measuring unit is provided in close relationship to the sensor medium.

The above described chemical sensor device has a high sensitivity and high selectivity towards analytes as well as a fast response and recovery time. A further subject of the invention therefore is a method for detecting an analyte in a sample, wherein a chemical sensor device as described above comprising a sensor medium and detection means is provided, the sample is applied to the sensor medium and a change of a physical and/or chemical property of the sensor medium is determined.

The above described chemical sensor devices are sensitive to different gases and organic vapour. They also may be used for detecting an analyte in a solution. A major advantage of the chemical sensor device according to the invention is its operation at or close to room temperature and its high sensitivity.

When using vanadium pentoxide nanofibres as a one-dimensional nanoparticles the chemical sensor device is sensitive to gases, say CO, $H_2$, $NH_3$ but also to $SO_x$, $O_2$ or $NO_x$. The sensor is highly sensitive to ammonia and polar organic molecules, like amines or thiols and detection below 0.5 ppm is possible. By changing the dopant, it is possible to create sensors with the same starting material, which cover the whole range of concentration for a given gas. The sensitivity towards amines allows an application of the sensor device according to the invention e.g. in the food industry to monitor food processing.

The response of $V_2O_5$-based sensors to gases is generally fast. The response time varies with the gas/vapour of interest as well as with the dopant. Even if the response can be slow, after 1 minute a large signal is already obtained, which is sufficient for electronic nose applications.

The reversibility of the signal is good. In most cases, 90% of the signal is recovered within 2-3 minutes when operated at room temperature.

With the sensor device according to the invention sensitivity increases with increasing relative humidity provided with the analyte in the case of amines. The detection occurs at a wide range of humidities. Humidity of at least 5% relative humidity can be used with values of at least 10% preferred and most preferably above 20% to ensure a sufficient signal.

To obtain reproducible results from the sensor device relative humidity level of the analytes is preferably kept at a constant level during the determination of the change of a physical property of the sensor medium.

The different effects that humidity has got on the sensitivity to different analytes can be used for identification of an analyte. The set-up consists in comparing the response to an analyte by humidifying it and by drying it. For example, humidity has little effect on the sensitivity of $V_2O_5$ to propanol. So in such configuration, both responses should be similar. However, the response of $V_2O_5$ to an amine will be much larger when the analyte is humidified then when a drying agent is placed between the sample and the sensor. Therefore, differentiation between propanol and an amine with such set-up is straightforward.

The sensor device according to the invention is very sensitive towards, the detection of amines. It could be demonstrated by the inventors that it is possible to detect amines in low concentrations down to 30 ppb at high humidity. Biogenic amines are often encountered in fermented foodstuff. For example, trimethylamine or ammonia is produced during fish decomposition. Therefore volatile amines may be used as indicator of fish freshness. Wine also contains volatile amines. Their influence can be limited to spoiling the taste of the wine, but more seriously, can also endanger the health of the consumer. With the method according to the invention detection of those volatile amines is easy to perform. Further also detection of volatile amines in body fluids, e.g. sweat, urine, breath or blood is possible and therefore the method for detecting an analyte, preferably an amine, according to the invention may be used for medical diagnosis. For example, di- and trimethylamine in the breath of a patient are indicative of uremic disease (kidney failure). Breast cancer can also be diagnosed by a specific pattern of volatile amines in urine. In addition, ammonia is often used in the chemical industry and the detection method according to the invention may be used to detect leaks.

A sensor device according to the present invention can detect concentrations 30 ppb of an amine, including a volatile amine, or ammonia in a sample at a humidity of at least 5% relative humidity. Humidity of at least 10% is preferred and most preferably humidity of at least 20% to ensure a sufficient signal. The concentration of amine or ammonia can be detected at concentrations of less than 100 ppm, 10 ppm or 1 ppm at a humidity of at least 5%, 10% or 20%.

Humidity has little effect on the response towards carbon monoxide, acetic acid and 1-propanol as could be demonstrated with vanadium pentoxide sensors. There was little loss of sensitivity to other analytes than amines at high humidity compared to dry conditions. This is a major advantage when an array of sensors containing some vanadium pentoxide sensors is used to analyze a complex smell.

BRIEF DESCRIPTION OF THE DRAWINGS

The invention will now be described in more detail by way of examples and with reference to the accompanying figures.

DETAILED DESCRIPTION

Figure 1:
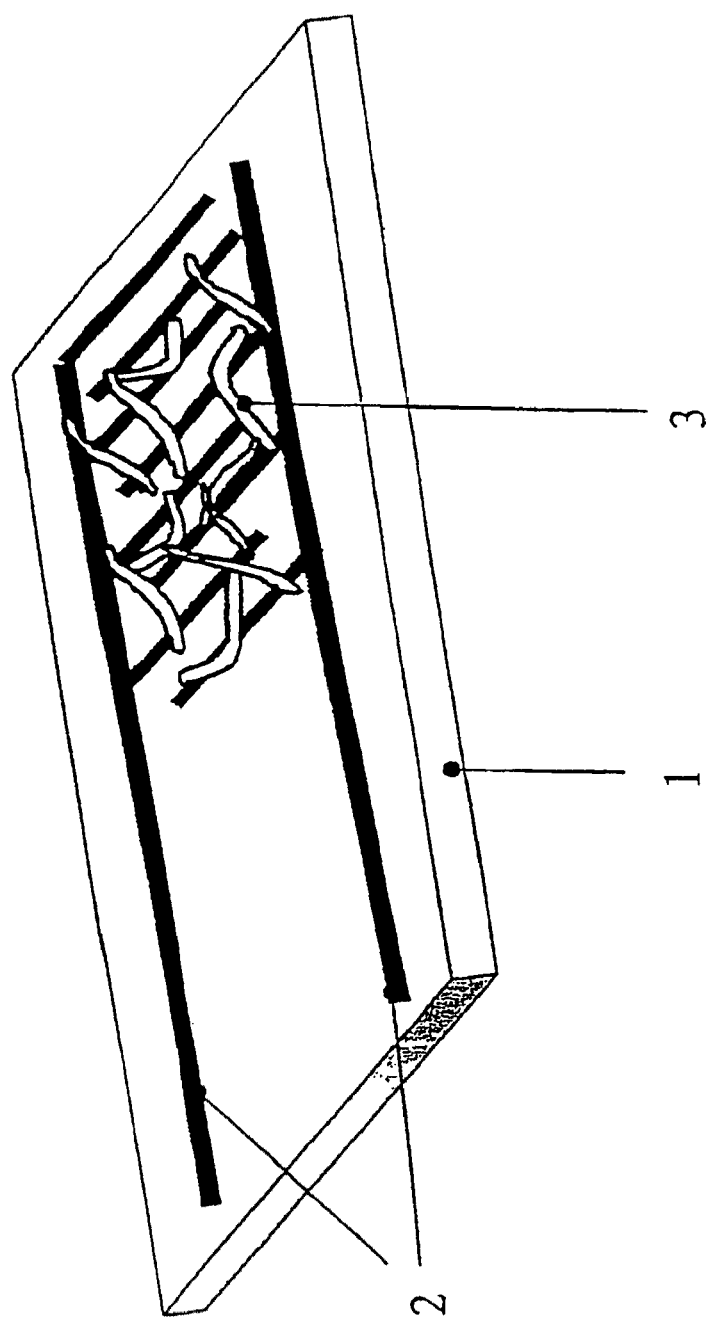
FIG. 1 shows schematically an assembled chemiresistor.

FIG. 1 schematically shows a chemiresistor, which has a sensor medium comprising one-dimensional nanoparticles (nanobelts) as a sensitive material. On a substrate 1 are placed interdigitated electrodes 2. The electrode structures 2 are covered by a sensor film, which is formed of one-dimensional nanoparticles 3. A constant current may be applied to the leads of the electrodes 2 and a change in the voltage across the electrodes may be detected by a detector (not shown).

Figure 2:
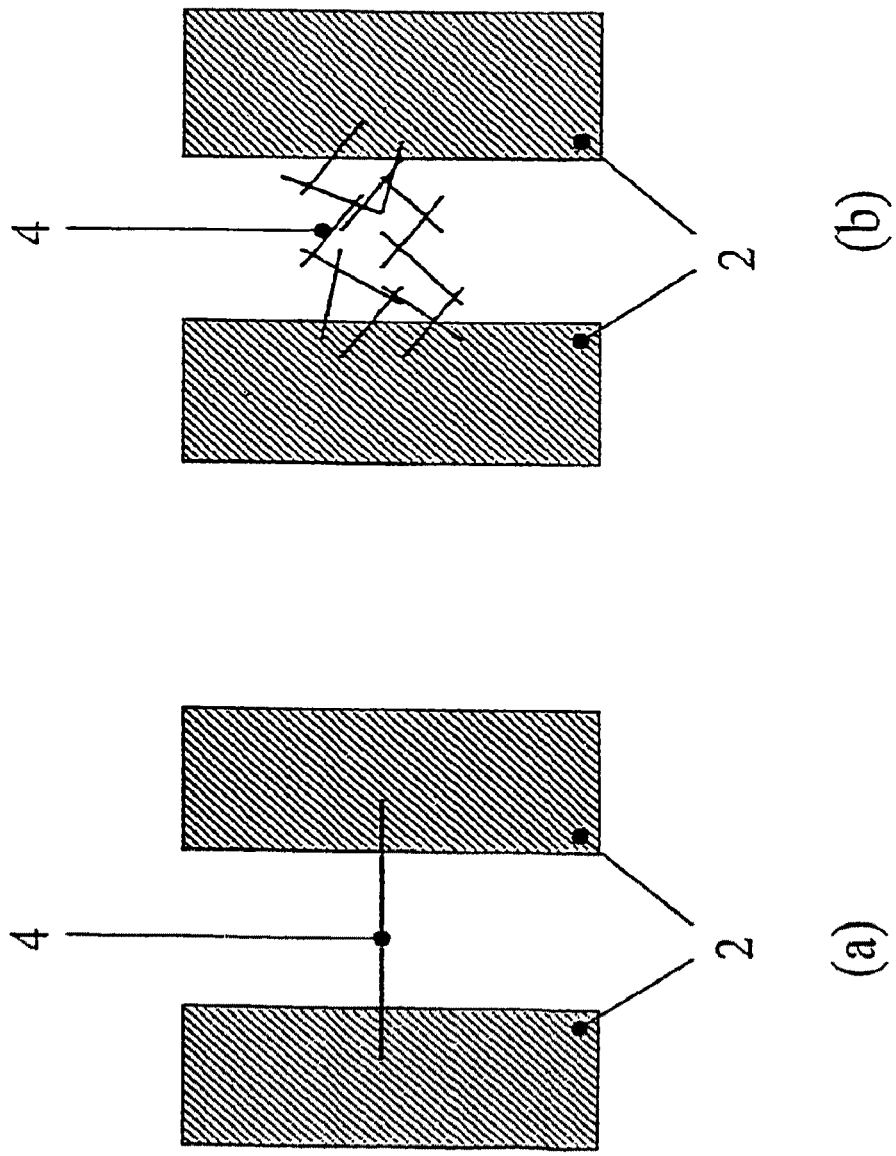
FIG. 2 schematically displays different types for the arrangement of one-dimensional nanoparticles to bridge a gap between a pair of electrodes.

FIG. 2 displays different arrangements of one-dimensional nanoparticles 4 between a pair of electrodes 2. In FIG. 2a a single one-dimensional nanoparticle 4 is bridging the gap between the pair of electrodes 2. For simplicity only one one-dimensional nanoparticle is shown on the figure. Several particles can also be employed. In this arrangement, the analyte can modulate the conductivity along the one-dimensional nanoparticle by adsorption on its surface and/or by intercalation. The analyte can also influence the conductivity of the device by affecting the conduction path between the particles 4 and the electrodes 2. The arrangement shown in FIG. 2a is preferred for detecting analytes mainly interacting with the particles changing the intrinsic conductivity of the one-dimensional particles. The one-dimensional nanoparticles can have a length much smaller than the gap size between a pair of electrodes. The one-dimensional nanoparticles are then arranged in a random order to form a network of nanoparticles 4 between a pair of electrodes 2 as shown in FIG. 2b. Like in the arrangement of FIG. 2a the analyte can affect the intrinsic conductivity of the particles as well as the contact resistance between the particles and the electrodes. In addition, the analyte can change the interparticle contacts. In this arrangement the analyte enhances or reduces the conduction between the nanoparticles. The arrangement shown in FIG. 2b is preferred when the analyte interacts with the interparticle contacts. Between individual one-dimensional nanoparticles 4 are formed voids, which provide an easy access of the analyte to the nanoparticle surface even when a sensor medium of a larger thickness is used.

Figure 3:
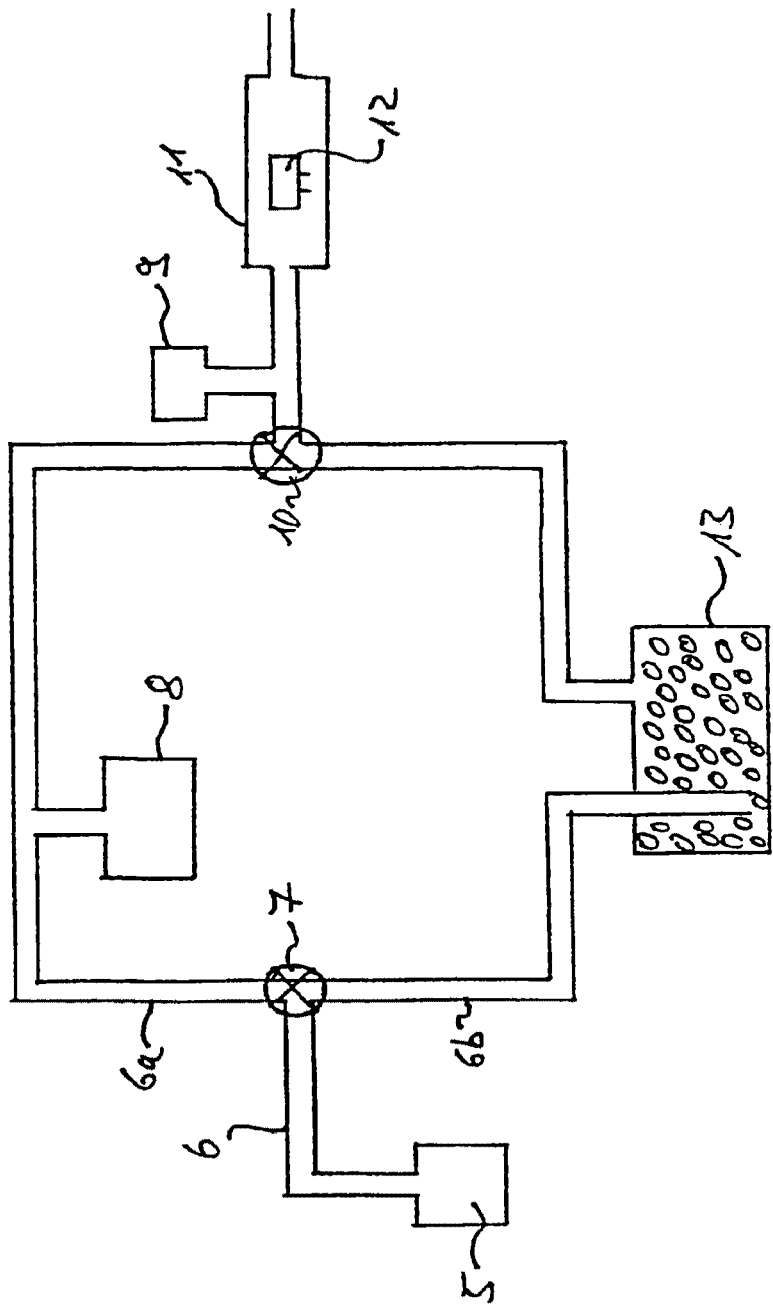
FIG. 3 schematically displays a set-up of a sensor device identification of different analytes by varying humidity of an analyte gas.
Figure 4:
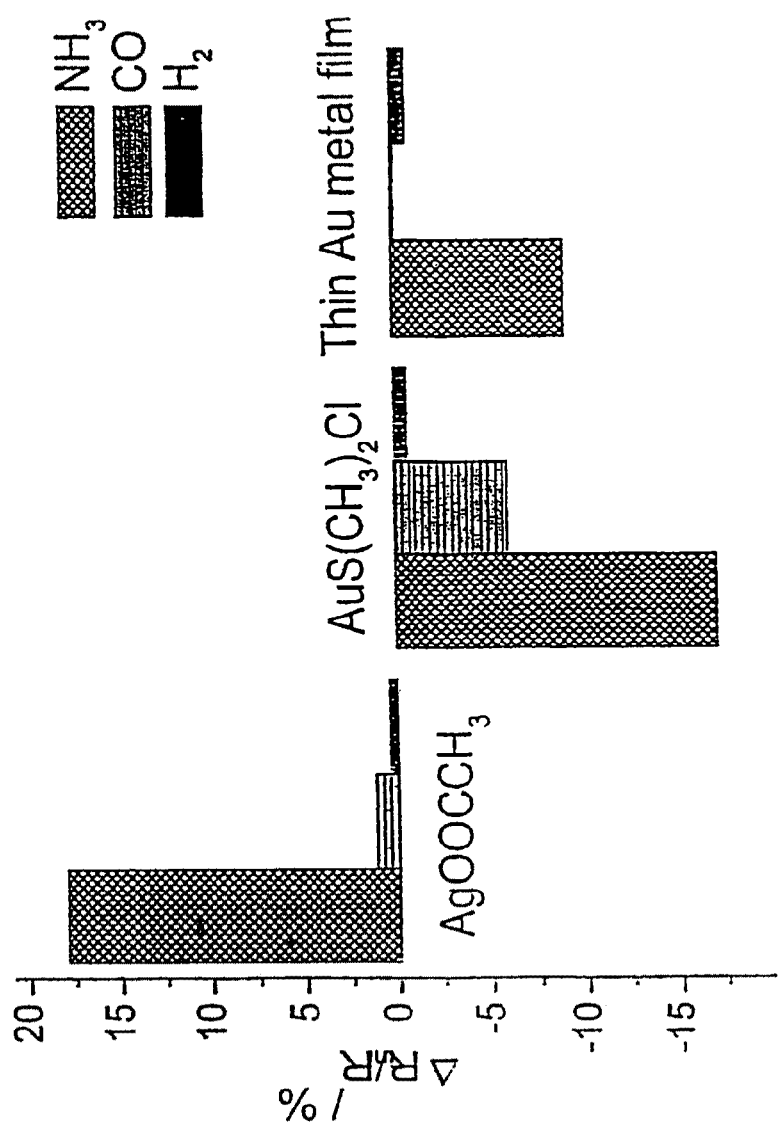
FIG. 4 shows the response of different sensors to 100 ppm analytes $NH_3$, CO and $H_2$.

FIG. 3 schematically displays a sensor device, which utilizes the influence of humidity on the sensitivity of the sensor towards different analytes. In a sample reservoir 5 an analyte is provided, comprising various compounds, e.g. an amine and propanol. From the sample reservoir 5 the analytes are transported by an carrier gas stream, e.g. a nitrogen stream, through a line 6 to a three-way valve 7. In a first step the three-way valve 7 is open towards line 6a, whereas line 6b is shut. The gas stream containing the analytes is passing a humidity control device 8 by which a defined humidity is adjusted. The humidity of the gas stream is monitored by a humidity-monitoring unit 9. The humidified gas stream passes a further three-way valve 10 and is then introduced into sensor chamber 11, where first signal is detected by sensor 12. Sensor 12 is connected to a computer (not displayed), that acts as a detecting device for storing and comparing the detected signals. Line 6b is shut by further three-way valve 10 and no gas is introduced into line 6b. In a second step three-way valves 7 and 10 are switched in such a way that line 6a is shut whereas line 6b is opened. The gas stream containing the analytes is now introduced into a drying unit 13 and dried for example by a drying agent. The dry gas stream is then introduced into sensor chamber 11 and a second signal is detected by sensor 12. In case humidity has little influence on the sensitivity of the sensor 12 towards propanol but has a large influence on the sensitivity of sensor 12 towards amines comparing first and second signal can differentiate those compounds. Whereas almost no difference is obtained in case of propanol a clear difference in intensity between both signals can be seen in case of an amine.

a) Preparation of Undoped Vanadium Pentoxide Nano-belts:

A wet-chemical method previously described by J. Muster et al. loc. cit. was used to prepare a stock of undoped $V_2O_5$ nanofibres. $V_2O_5$ sols were prepared from 0.2 g ammonium (meta)vanadate (Aldrich) and 2 g acidic ion exchange resin (Dowex 50WX8-100, Aldrich) in 40 mL water. After a few hours the formation of an orange sol is observed that darkens with time. $V_2O_5$ fibers with length of a few micrometers were observed after about 3 days. The fibers employed for the experiments were several months old.

b) Preparation of Silver Doped Vanadium Pentoxide Nano-belts

Silver doped vanadium pentoxide nanofibres were prepared as described under (a) but during preparation of the $V_2O_5$ sols a silver salt (silver nitrate) is added to the solution.

The silver doped vanadium pentoxide nanofibres were used to prepare sensor 7.

c) Fabrication of Sensors:

The one-dimensional nanoparticles were deposited onto BK7 glass substrates supporting lithographically made interdigitated electrode structures. The electrode structures comprised a 5 nm titanium adhesion layer on which a 95 nm gold layer was deposited. They comprised 50 finger pairs having a width of 10 µm, a spacing of 10 µm, and an overlap of 1800 µm. The overall size of the electrode structures was 2 mm by 2 mm. Before depositing the sensor film, the substrates were cleaned in an ultrasonic bath with acetone, hexane, and iso-propanol and by applying an oxygen plasma (4 min at 30 W and 0.24 mbar). The cleaned substrates were immersed into a solution of 0.1% DAS (N-[3-(trimethoxysilyl)propyl]-ethyl-enediamine, Aldrich) in water for two minutes followed by thorough rinsing with pure water and drying under a stream of air. This procedure functionalized the glass substrates with amino groups, which served as linking groups for subsequent nanofibre deposition. Fibers obtained under (a) were dip coated onto the substrate by dipping the substrate for 20 secs. in a diluted suspension of the fibers in $H_2O$. The substrates were rinsed with pure water and dried in a stream of air. Undoped $V_2O_5$-nanofibre sensors (sensor 8) ere obtained in this way.

d) Fabrication of a Silver-Doped Sensor (Sensor 7)

The fabrication procedure described under (c) was repeated but as one-dimensional nanoparticles were used silver doped vanadium pentoxide nanofibres obtained under (b). Thereby a silver doped $V_2O_5$-nanofibre sensor was obtained as sensor 7.

e) Doping of Sensors by Dipping

Sensors obtained under (c) were dipped into a solution of the dopant as detailed in table 1. After dipping the sensors were thoroughly rinsed with pure water and dried in a stream of air.

TABLE 1

Sensors obtained by dipping in a dopant solution

| Sensor | Dopant | [Dopant] | Solvent | Exposure time |
|---|---|---|---|---|
| 1 | Silver acetate | 1 mg in 1 ml | $H_2O$ | 10 secs. |
| 2 | $AuS(CH_3)_2{}^+Cl^-$ | 1 mg in 1 ml | NMF | 20 min |
| 4 | $AuCl_3$ | 1 mg in 1 ml | NMF | 30 min |
| 5 | Silver acetate | 0.1 mg in 1 ml | $H_2O$ | 10 secs. |
| 6 | Silver acetate | 10 mg in 1 ml | $H_2O$ | 10 secs. | f) Doping of Sensor by Evaporation of a Gold Layer (Sensor 3)

Evaporation of a gold layer of 2 nm thickness on an undoped sensor obtained under (c). resulted in sensor 3. Atomic force microscopy showed that approximately spherical particles were formed.

g) Sensitivity of Sensors to Different Gases

For gas test experiments, the sensors prepared as described under (c)-(f) were placed in a home made teflon chamber having a volume of about 1.23 cm$^3$. The test gas was prepared by diluting a stock of an analyte (10% analyte ($H_2$, CO, $NH_3$) in $N_2$) with an appropriate amount of carrier gas (dry $N_2$) using a mass flow system MK5 from MCZ Umwelttechnik GmbH, Ober-Morlen, Germany to obtain the desired analyte concentration. The mass flow in the test chamber was adjusted to 400 mL/min. and kept constant for all experiments. All experiments were done at room temperature.

The resistance was monitored by applying a dc current using a SMU 236 (Keithley) and recording the voltage using a multimeter 2002 (Keithley). The relative change in resistance was measured 120 secs. after exposing the sensors to the gas of interest.

TABLE 2

Response $\Delta R/R_{ini}$ of sensors 1-4 to different gases

|  | 100 ppm $NH_3$ | 100 ppm CO | 100 ppm $H_2$ |
|---|---|---|---|
| Sensor 1 | +18% | +1.2% | +0.4% |
| Sensor 2 | −17% | −6% | −0.7% |

TABLE 2-continued

Response $\Delta R/R_{ini}$ of sensors 1-4 to different gases

|  | 100 ppm $NH_3$ | 100 ppm CO | 100 ppm $H_2$ |
|---|---|---|---|
| Sensor 3 | −9% | −1.2% | −0.8% |
| Sensor 4 | +13% | +1.6% | +0.2% |

The responses of sensors 1-3 are also graphically displayed in FIG. 3. Whereas sensors 1 and 2 have about the same sensitivity to ammonia (in absolute value), sensor 2 has a sensitivity towards CO which is about 5 times larger than for sensor 1. By combining these two sensors it is therefore possible to distinguish $NH_3$ and CO. Sensor 3 is less sensitive to ammonia than sensors 1 and 2, but is more sensitive to $H_2$. This makes this sensor more suitable for applications where detection of hydrogen is required.

h) Influence of Doping Level

Figure 5:
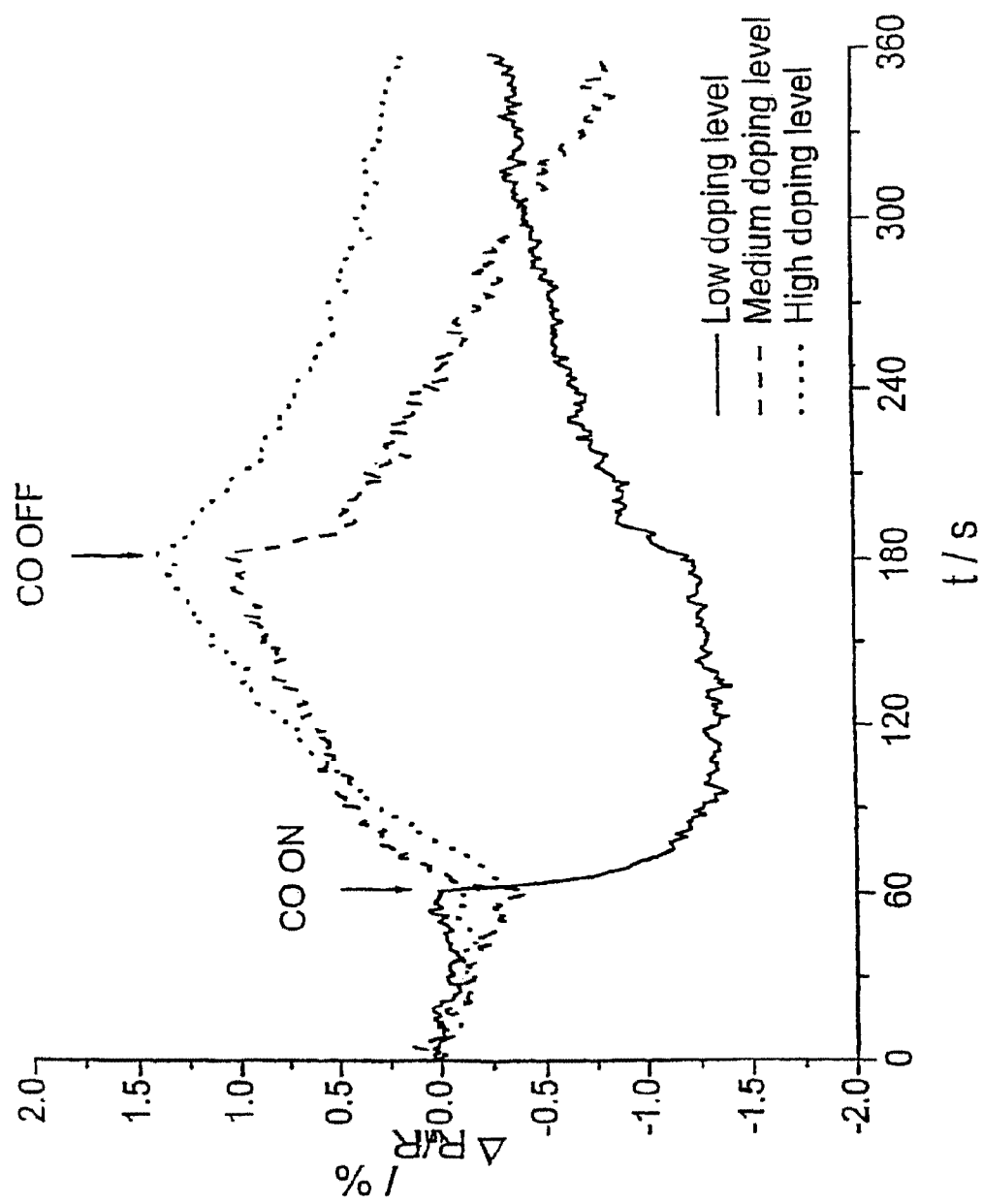
FIG. 5 shows a response of a silver doped vanadium pentoxide sensor to 100 ppm CO at different doping levels of the sensor medium at room temperature.

Silver doped vanadium pentoxide sensors 1, 5 and 6 having low (sensor 5), medium (sensor 1) and high (sensor 6) doping level were exposed to 100 ppm CO. The response of the sensors is displayed in FIG. 5. Whereas sensor 5 displayed a fast response and a change in relative resistivity $\Delta R/R_{ini}$ of −1.3% sensors 1 and 6 having medium and high doping level displayed a change in relative resistivity $\Delta R/R_{ini}$ of +1.0% and +1.3, respectively. This demonstrates that the response of the sensor can be modified by varying the doping level.

i) Sensitivity of Silver Doped Vanadium Pentoxide Sensors Toward $NH_3$

Figure 6:
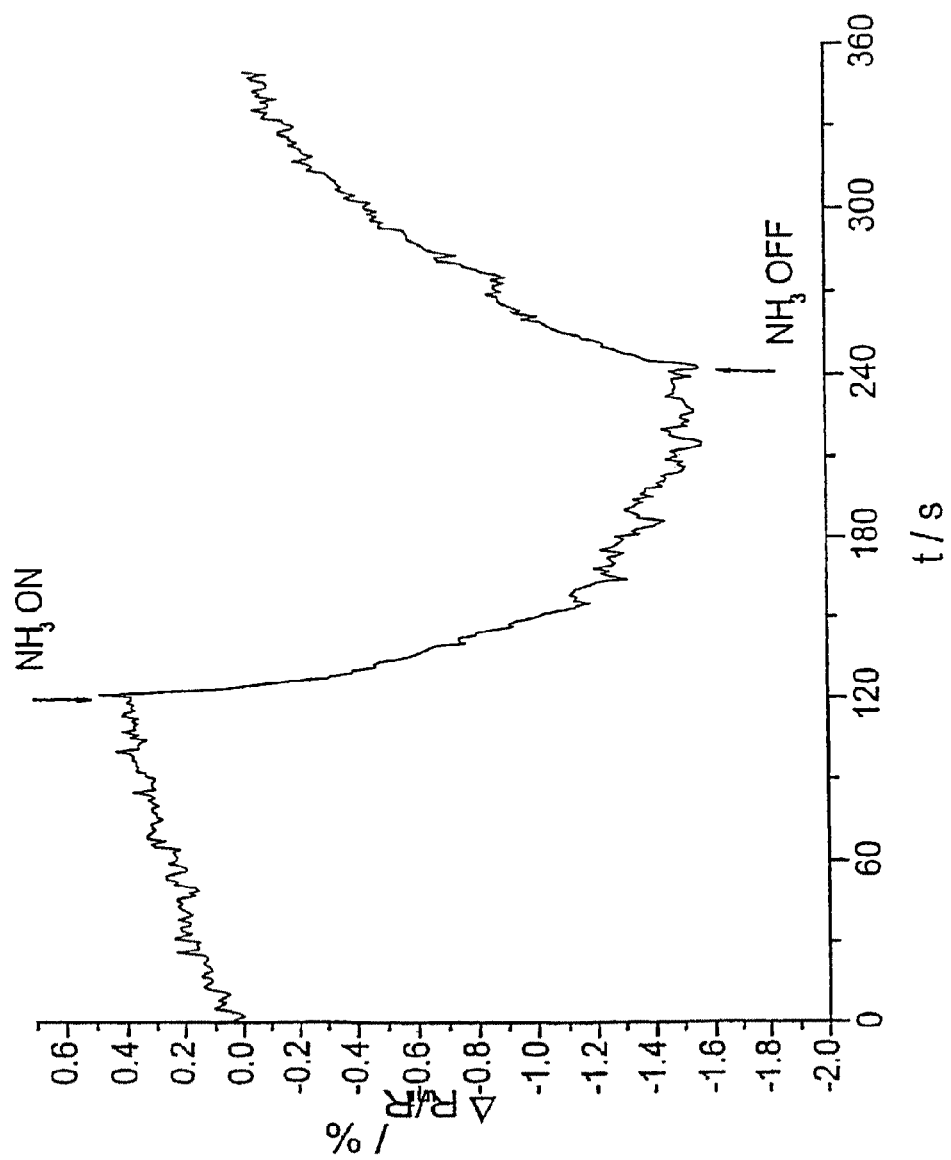
FIG. 6 shows a response of a silver doped vanadium pentoxide sensor (sensor 7) to 360 ppb $NH_3$ at room temperature.
Figure 7:
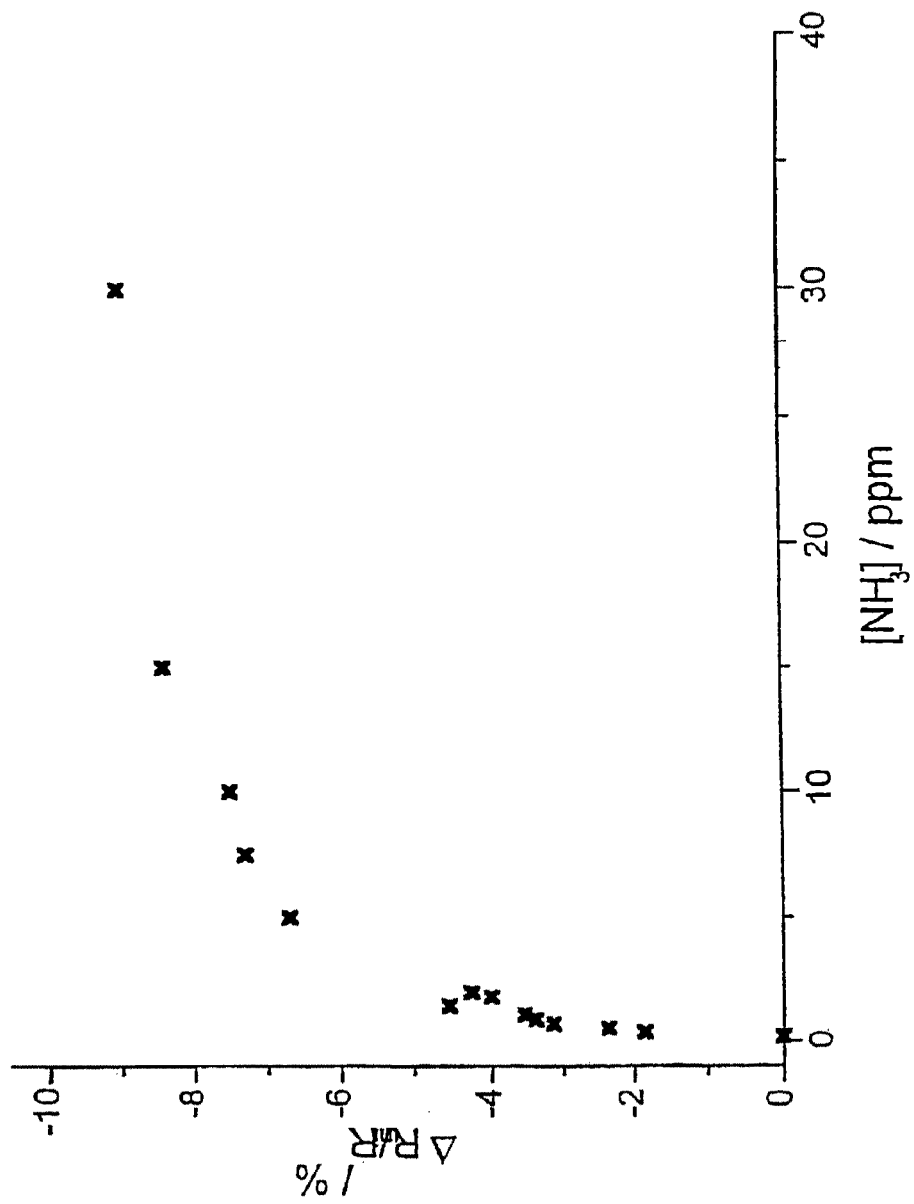
FIG. 7 shows the sensitivity isotherm of a silver doped vanadium pentoxide sensor (sensor 7) to $NH_3$ at room temperature.

Sensor 7 was exposed to 360 ppb ammonia. The response of the sensor is displayed in FIG. 6. The sensor displayed a fast response of $\Delta R/R_{ini}$-1.6% within 120 seconds. This demonstrates that the sensor is sensitive to very low concentrations of ammonia giving a fast response and a short recovery period. At higher ammonia concentrations an increased response of the sensor is obtained as is obvious from the sensitivity isotherm displayed in FIG. 7.

k) Sensitivity Towards Carbon Monoxide

Figure 8:
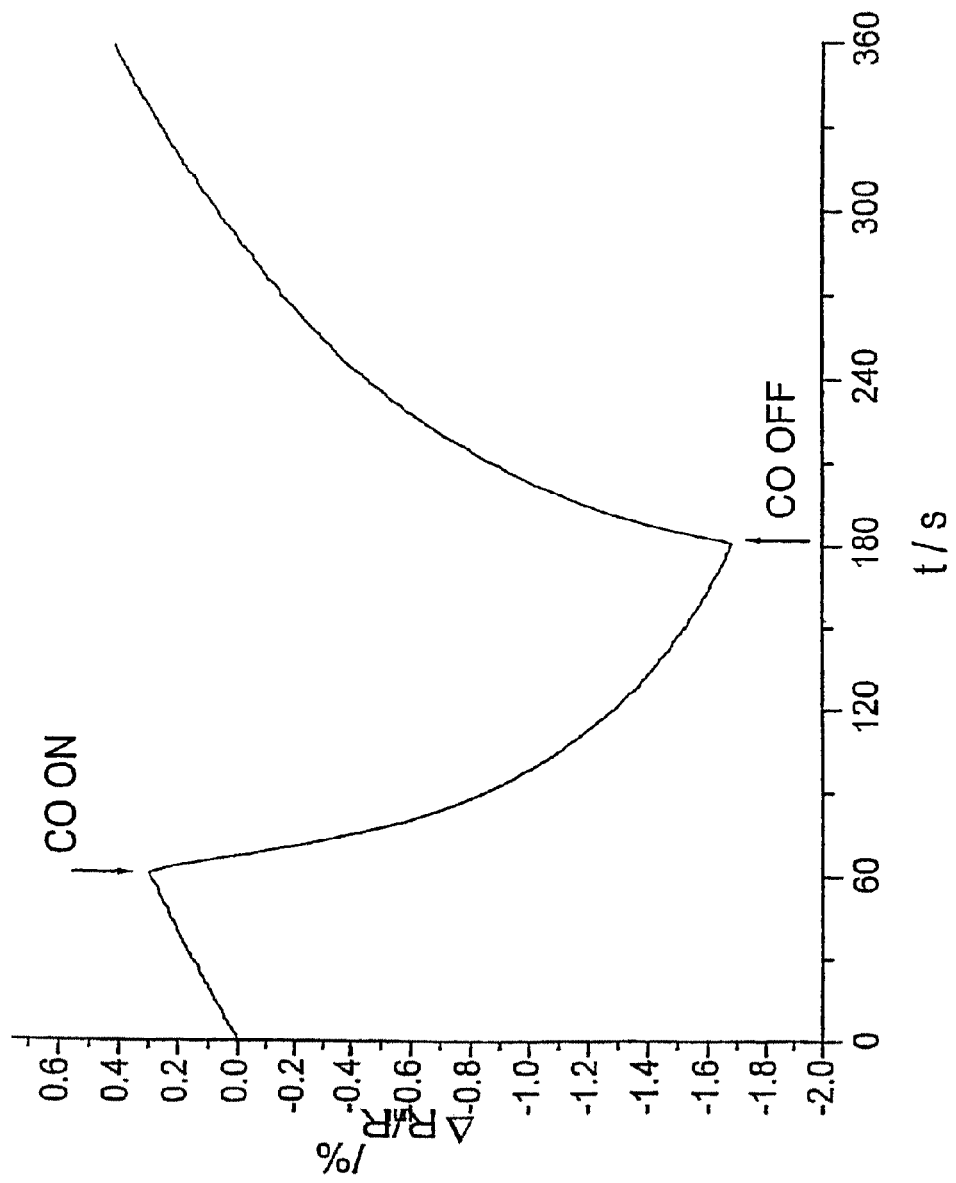
FIG. 8 shows the response of a vanadium pentoxide sensor doped with gold (sensor 2) to 1 ppm CO at room temperature.

Gold doped sensor 2 was exposed to 1 ppm CO at room temperature. The response of the sensor is displayed in FIG. 8. Even at low concentration a response $\Delta R/R_{ini}$ of −1.7% was obtained within 120 seconds.

l) Sensitivity Towards Hydrogen Gas

Figure 9:
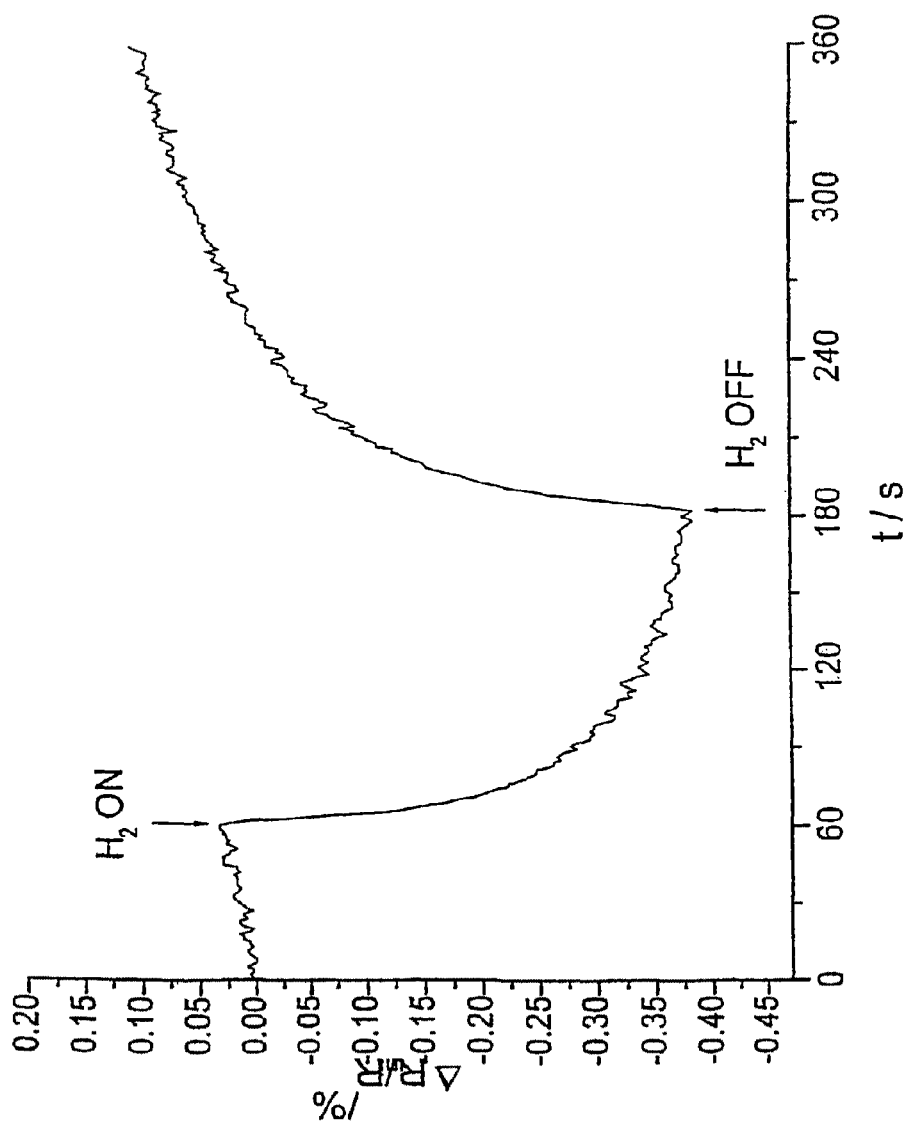
FIG. 9 shows the response of another vanadium pentoxide sensor doped with gold (sensor 3) to 20 ppm $H_2$ at room temperature.

Gold doped sensor 3 was exposed to 20 ppm $H_2$ at room temperature. The response of the sensor is displayed in FIG. 9. Within 120 secs. a response $\Delta R/R_{ini}$ of −0.4 was obtained.

The vanadium pentoxide based sensors can be used as single sensor for $NH_3$, CO and $H_2$. Due to the cross-sensitivity to different gases and to the different selectivities of the different sensors, an array of $V_2O_5$-based sensors with different dopants can be used as an array of sensors for electronic noses.

m) Sensitivity Towards Butylamine at High Humidity

Figure 10:
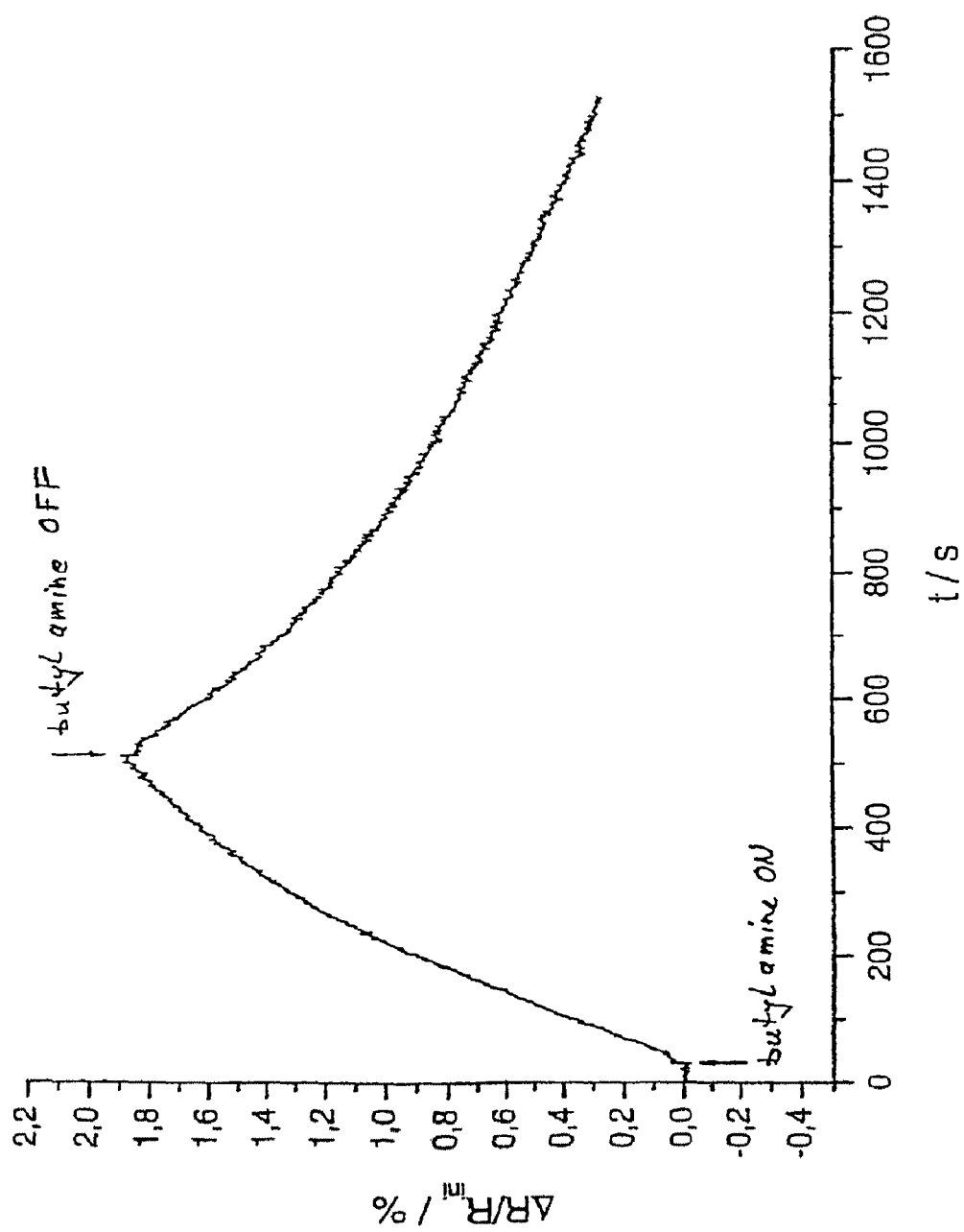
FIG. 10 shows the response of a silver-doped vanadium pentoxide chemoresistor to 30 ppb butylamine at 40% relative humidity.

Silver doped sensor 7 was exposed to 30 ppb butylamine at 40% relative humidity. The response of the sensor is displayed in FIG. 10. The arrow up shows when the butylamine is applied and the arrow down shows when the butylamine is removed from the gas phase. Within 500 secs. a response $\Delta R/R_{ini}$ of 1.9% was obtained.

n) Detection of Biogenic Amines

Figure 11:
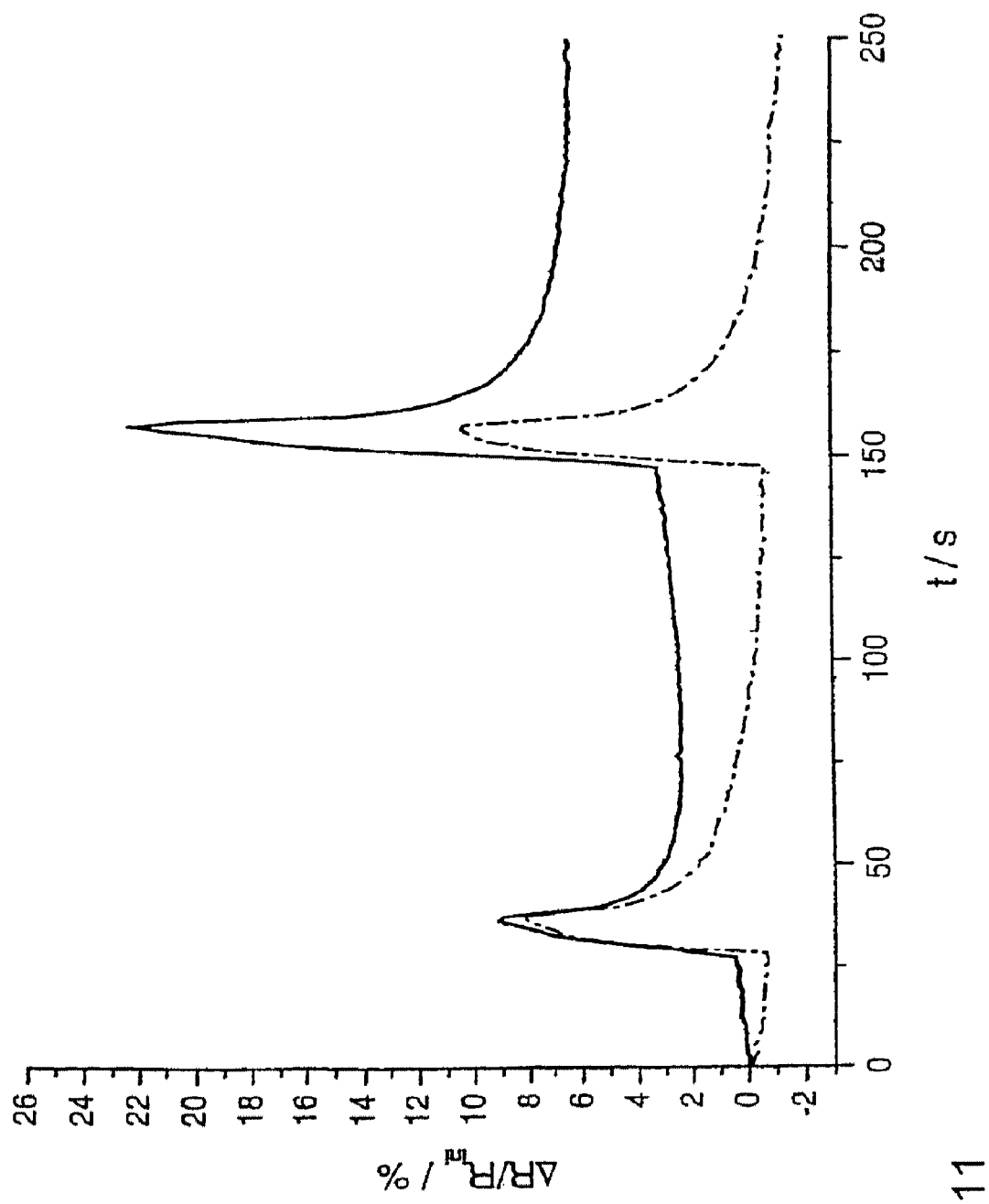
FIG. 11 shows the response of a silver-doped vanadium pentoxide chemoresistor to fish samples (cod)

Two fresh fish samples (cod) where prepared and stored in glass containers each. The gas of the head space was sampled by using a micropump and analyzed by exposing it to silver doped sensor 7 for 10 seconds each. First sample 1 was analyzed followed by sample 2. The dotted line displayed in FIG. 11 is the trace recorded at one day when the samples were fresh. Both samples gave similar signals. Sample 1 was then stored in a fridge for 24 hours whereas sample 2 was stored at ambient conditions. Both samples were again analyzed the next day. The plain line displayed in FIG. 11 corresponds to the trace recorded after storage of the samples. The signal of sample 2, stored under ambient conditions, gives a larger response than the signal of sample 1 stored in the fridge. It is known that most sea fishes produce amines during decomposition. We assign the increase in signal of sample 2 to a faster decomposition of the fish due to the elevated storing temperature, and therefore a higher level of amine.

o) Influence of Humidity on Sensor Sensitivity

Figure 12:
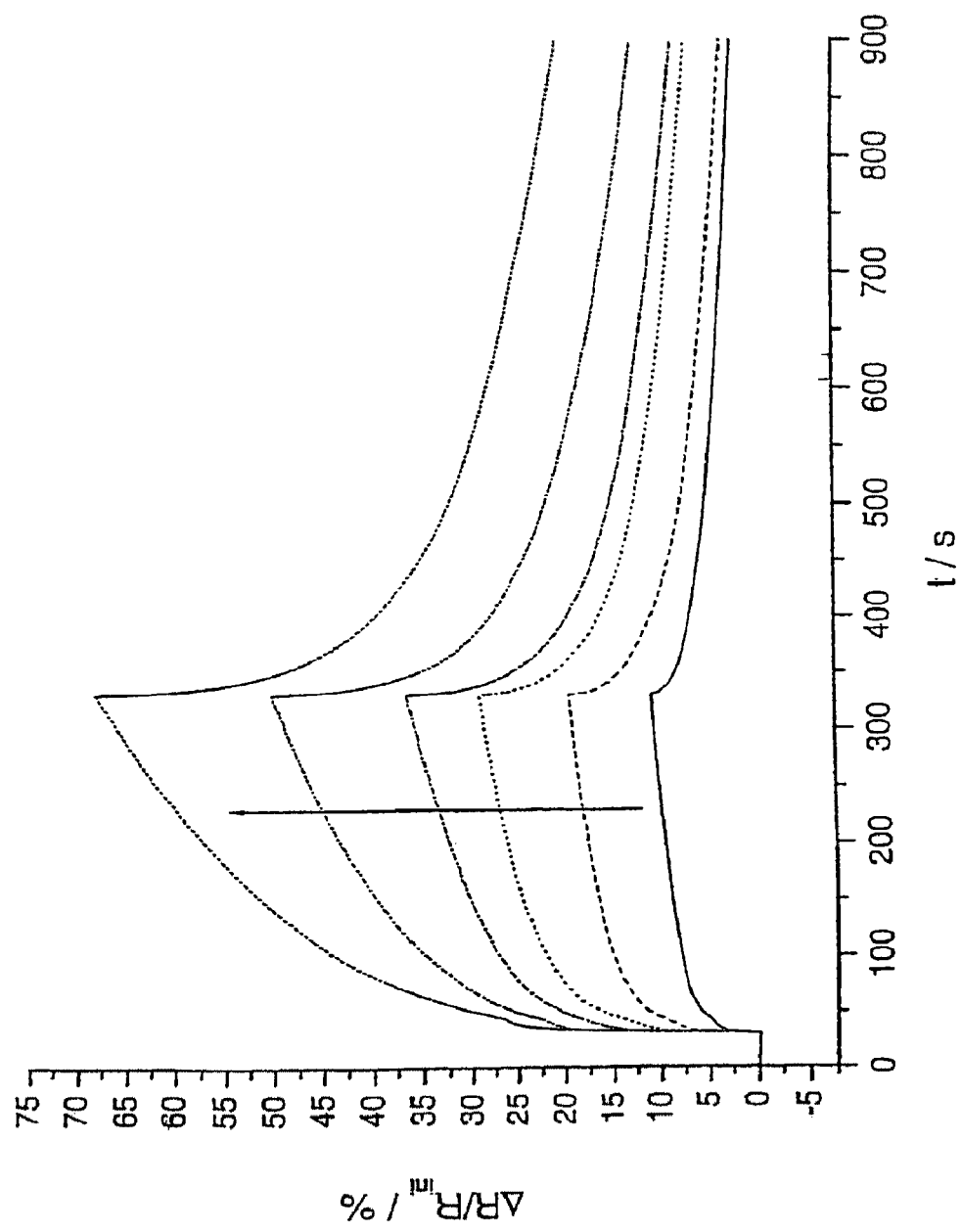
FIG. 12 shows the response of a silver-doped vanadium pentoxide chemoresistor to 237 ppm butylamine at different relative humidities.

Silver doped sensor 7 was exposed to 237 ppm butylamine at different humidities. The sensor response was measured at 5, 20, 30, 40, 50 and 60% relative humidity. The response of the sensor is displayed in FIG. 12. The arrow indicates the increasing humidity. The highest level of sensitivity was obtained at 60% relative humidity.

What is claimed:

1. Method for forming a chemical sensor device, comprising:
    a) providing a substrate having a substrate surface;
    b) providing one-dimensional nanoparticles essentially consisting of a semiconducting AxBy compound, wherein the semiconducting AxBy compound comprises vanadium pentoxide (V205) having a shape of a fiber or a filament with a cross-section of less than 100,000 nm2;
    c) coating the substrate surface with the one-dimensional nanoparticles thereby obtaining a sensor medium; and
    d) providing detection means for detecting a change of conductivity of the sensor medium.

2. Method according to claim 1, wherein the one-dimensional nanoparticles are aligned on the substrate surface.

3. Method according to claim 1, wherein the one-dimensional nanoparticles are fixed to the substrate surface by a bifunctional ligand that is linked to the substrate surface by a first functional group and to the one-dimensional nanoparticle surface by a second functional group.

4. Method according to claim 1, wherein a humidity control device and/or a humidity measuring unit is provided in close relationship to the sensor medium.

5. The method of claim 1, wherein the filament or fiber has a length of less than 100 μm.

* * * * *